| United States Patent [19] | [11] Patent Number: 4,906,654 |
| Gillard et al. | [45] Date of Patent: Mar. 6, 1990 |

[54] CYCLOHEPT[B]INDOLEAKANOIC ACIDS, PHARMACEUTICAL COMPOSITIONS AND USE

[75] Inventors: John W. Gillard, Baie d'Urfe; Howard E. Morton, Dollard des Ormeaux; Yvan Guindon, Montreal; Yves Girard, Ile Bizard; Christiane Yoakim, Montreal, all of Canada

[73] Assignee: Merck Frosst Canada, Inc., Kirkland, Canada

[21] Appl. No.: 211,800

[22] Filed: Jun. 27, 1988

Related U.S. Application Data

[63] Continuation of Ser. No. 76,096, Jul. 21, 1987, Pat. No. 4,775,680.

[51] Int. Cl.$^4$ .................. A61K 31/40; C07D 209/86; C07D 209/88

[52] U.S. Cl. .................... 514/411; 548/434; 548/448

[58] Field of Search ................ 548/439, 448; 514/411

[56] References Cited

U.S. PATENT DOCUMENTS 4,009,181 2/1977 Berger et al. ...................... 548/448
4,057,559 11/1977 Asselin et al. ...................... 548/439

Primary Examiner—Robert W. Ramsuer
Attorney, Agent, or Firm—Gabriel Lopez; Hesna J. Pfeiffer

[57] ABSTRACT

Cyclohept[b]indolealkanoic acids and acid derivatives are disclosed. The compounds act as prostaglandin and thromboxane antagonists and are useful in treating asthma, diarrhea, hypertension, angina, platelet aggregation, cerebral spasm, premature labor, spontaneous abortion, dysmenorrhea and nephrotoxicity caused by cyclosporin A and as cytoprotective agents.

10 Claims, No Drawings

CYCLOHEPT[B]INDOLEAKANOIC ACIDS, PHARMACEUTICAL COMPOSITIONS AND USE

This is a continuation of application Ser. No. 076,096, filed July 21, 1987, now U.S. Pat. No. 4,775,680.

BACKGROUND OF THE INVENTION

This invention relates to prostaglandin antagonists useful in treating a variety of conditions, such as allergic asthma where excessive contractile activity of prostaglandins and prostaglandin biosynthetic intermediates occur.

These compounds antagonize the actions of contractile prostaglandins, such as $PGF_{2\alpha}$, $PGG_2$, $PGH_2$, $PGD_2$ and $TXA_2$. The use of agents which act as prostaglandin antagonists offers new approaches to therapy in a number of disease states. For example, certain prostaglandins, such as $PGF_{2\alpha}$, $PGD_2$, $PGG_2$, and $PGH_2$, are potent bronchospastic agents. Indeed human asthmatics have been shown to be especially sensitive to the bronchial constricting action of $PGF_{2\alpha}$.

The compounds of the present invention are also antithrombotic agents. Thus, they are useful in the treatment and/or prevention of thromboembolic diseases such as arterial thrombosis and those involving platelet deposition, e.g. prothesis.

In addition to the involvement of contractile prostaglandins in asthma, prostaglandins are known to play a role in other allergic conditions, as well as, diarrhea, hypertension, angina, platelet aggregation, cerebral spasm, cerebral ischemia, arrythmia, circulatory shock, sudden death, atherosclerosis, myocardial ischemia, premature labor, spontaneous abortion, dysmenorrhea, glomerular nephritis, and systemic lupus erythematosis. Consequently, the compounds of this invention will alleviate the above mentioned diseases.

The compounds of the present invention are also useful as agents for protection against the nephrotoxicity caused by cyclosporin A and related drugs.

In addition to the prostaglandin antagonist actions, the compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus inhibition of the synthesis of such compounds will alleviate these and other leukotriene-related disease states.

The compounds of the present invention may be used to treat or prevent mammalian (especially, human) disease states such as erosive gastritis; erosive esophagitis; ethanol-induced hemorrhagic erosions; hepatic ischemia; noxious agent induced damage or necrosis of hepatic, pancreatic, renal, or myocardial tissue; liver parenchymal damage caused by hepatotoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

Certain 9-benzyl-1,2,3,4-tetrahydrocarbazole acetic acids or esters thereof are shown as chemical intermediates in the preparation of carbazoles that are known in the art as anti-inflammatory, analgesic and anti-rheumatic agents (see U.S. Pat. No. 3,896,145 and British Pat. No. 1,385,620). Certain 9-benzyl-1,2,3,4-tetrahydrocarbazole carboxylic acids are known in the art as anti-inflammatory, analgesic and anti-rheumatic agents (see U.S. Pat. Nos. 3,868,387; 4,009,181; 3,905,998 and 3,758,496). None of these compounds, however, are shown to be prostaglandin, or thromboxane antagonists or inhibitors of leukotrine biosynthesis.

The specific class of compounds of the present invention, substituted 5-benzyl-5,6,7,8,9,10-hexahydrocyclohept[b]indolealkanoic acids, has not been previously described.

DESCRIPTION OF THE INVENTION

The present invention relates to novel compounds of Formula I:

[Chemical structure of Formula I showing substituted cyclohept[b]indole with substituents $R^1$, $R^2$, $R^3$, $R^4$ on the benzene ring fused at positions 1-4, $R^7$ on the cycloheptyl ring, $R^8$-CH at N-5, and a benzyl group with $R^5$, $R^6$ substituents, and group A]

wherein:

A is $-(CR^9R^{10})_rR^{11}$;

$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) $-(CH_2)_nM$ wherein n is 0 to 3 and M is
  (a) $-C(O)R^{15}$;
  (b) $-C(O)NR^{17}R^{17}$;
  (c) $-CN$;
  (d) $-C(O)R^{16}$;
  (e) $-C(O)CH_2OH$ (hydroxymethyl ketone);
  (f) $-CF_3$;
  (g) $-R^{14}$;
  (h) -tetrazole;
  (i) $-OR^{12}$;
  (j) $-OC(O)R^{16}$;
  (k) $-OC(O)NR^{17}R^{17}$;
  (l) $-OC(O)OR^{18}$;
  (m) $-SR^{13}$;
  (n) $-S(O)R^{13}$;
  (o) $-S(O)_2R^{13}$;
  (p) $-S(O)_2NR^{17}R^{17}$;
  (q) $-NR^{17}R^{17}$;
  (r) $-NHC(O)R^{16}$;
  (s) $-NHS(O)_2R^{13}$;
  (t) $-N_3$;
  (u) $-NO_2$;
  (v) $-$halogen.

each $R^7$ is independently H or $C_1$ to $C_6$ alkyl;

each $R^8$ is independently H or $C_1$ to $C_6$ alkyl;

each $R^9$ is independently H or $C_1$ to $C_6$ alkyl;

each $R^{10}$ is independently H, OH, $C_1$ to $C_4$ alkoxy or $C_1$ to $C_4$ alkyl;

$R^{11}$ is $-C(O)OR^{19}$; $-C(O)R^{20}$; $CH_2OH$; $CHO$; tetrazole; $-C(O)NHS(O)_2R^{13}$; $NHS(O)_2R^{13}$; $-C(O)CH_2OH$; $-C(O)NR^{17}R^{17}$ or $NHS(O)_2OH$;

each $R^{12}$ is independently H; $C_1$ to $C_6$ alkyl; benzyl; or $R^{14}$;

each $R^{13}$ is independently $C_1$ to $C_6$ alkyl, $CF_3$ or $R^{14}$;

each $R^{14}$ is independently phenyl, mono-substituted phenyl, or di-substituted phenyl wherein the substituents are independently, $C_1$ to $C_3$ alkyl, $C_1$ to $C_3$ perfluoroalkyl, $C_1$ to $C_3$ alkoxy, halogen, CN, —C(O)OR$^{15}$, or —CH$_2$—C(O)OR$^{15}$;

each $R^{15}$ is independently H, phenyl, benzyl or $C_1$ to $C_6$ alkyl;

each $R^{16}$ independently is H, $R^{13}$ or (CH$_2$)$_m$C(O)OR$^{15}$;

each $R^{17}$ is independently $R^{12}$, or two $R^{17}$ groups may be joined to form a 5- or 6-membered saturated ring optionally containing an oxygen atom or a second nitrogen atom, the latter being substituted by H or $C_1$ to $C_6$ alkyl;

each $R^{18}$ is independently $C_1$ to $C_6$ alkyl, benzyl or phenyl;

each $R^{19}$ is H, $C_1$ to $C_6$ alkyl, $R^{14}$, $R^{21}$ or $R^{22}$;

$R^{20}$ is —(CH$_2$)$_t$—C(R$^9$)$_2$—(CH$_2$)$_t$—R$^{23}$;

$R^{21}$ is —CH$_2$—R$^{14}$;

$R^{22}$ is —CH$_2$—CH$_2$—R$^{14}$ $R^{23}$ is (A) a monocyclic or bicyclic heterocyclic radical containing from 3 to 12 nuclear carbon atoms and 1 or 2 nuclear heteroatoms selected from N, S, or O and with each ring in the heterocyclic radical being formed of 5 to 6 atoms, or (B) the radical W-R$^{24}$;

$R^{24}$ contains up to 21 carbon atoms and is (1) a hydrocarbon radical or (2) an acyl radical of an organic acyclic or monocyclic carboxylic acid containing not more that 1 heteroatom in the ring;

W is O, S or NH;

m is 0 to 4 r is 0 to 6 t is 0 to 3

The esters defined by $R^{20}$ are intended to include the esters such as are described by Saari, et al, J. Med. Chem., 21, 746–753 (1978) and Sakamoto, et al, Chem. Pharm. Bull., 32, 2241–2248 (1984) which are hereby incorporated by reference; or a pharmaceutically acceptable salt thereof.

Certain functional groups are represented by conventional short forms. Representative examples are shown below with the full bonding indicated.

| Structural representation of Functional Groups | | |
|---|---|---|
| Group No. Name | Convention used | Full bonding |
| 1. carboxy | —CO$_2$H | O‖—C—OH |
| 2. carboxylic acid ester | —C(O)OR$^{15}$ | O‖—C—O—R$^{15}$ |
|  | —OC(O)R$^{16}$ | O‖—O—C—R$^{16}$ |
| 3. carboxylic acid amide | —C(O)NR$^{17}$R$^{17}$ | O R$^{17}$‖ \|—C—N—R$^{17}$ |
| 4. ketone or aldehyde | —C(O)R$^{16}$ | O‖—C—R$^{16}$ |
| 5. aldehyde | —CHO | O‖—C—H |
| 6. sulfoxide | —S(O)R$^{13}$ | O‖—S—R$^{13}$ |

| -continued | | |
|---|---|---|
| Structural representation of Functional Groups | | |
| Group No. Name | Convention used | Full bonding |
| 7. sulfone | —S(O)$_2$R$^{13}$ | O‖—S—R$^{13}$‖O |

As used herein, the terms "each independently" or the equivalents thereof are employed to describe a number of possible position isomers and/or structural variations. For example, as described above, the following unit is attached to of the cyclohept[b]indole ring:

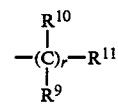

The letter r represents possible alkane chains of from 0 to 6 carbon atoms, each having the $R^9$ and $R^{10}$ substituent groups. On each carbon atom of the alkane chain, the $R^9$ and/or $R^{10}$ substituent may be different. The above description therefore contemplates structures such as the following for the segment —(CR$^9$R$^{10}$)$_r$—:

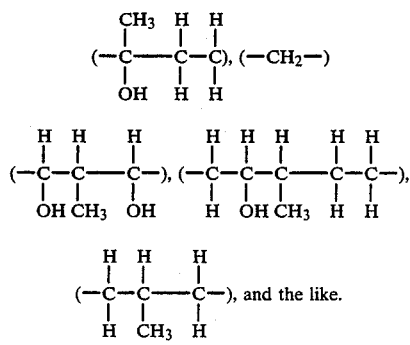

If an $R^{10}$ is OH and $R^{11}$ is CO$_2$H, such compounds may form a lactone, and such lactones are to be regarded as part of the present invention.

The alkyl groups referred to above may be straight chain or branched or may include cycloalkyl groups. As used herein, the term "lower" as applied to alkyl, acyl, alkoxy and the like, unless stated otherwise refers to groups having 1 to 6 carbon atoms. Halogen or halo means fluoro, chloro, bromo and/or iodo.

Pharmaceutically acceptable salts of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, tri-methylamine, diethanolamine, diethylamine, triethylamine, tripropylamine, ethanolamine, 2-dimethylaminoethanol, 2-diethylamino-ethanol, tomethamine, lysine, arginine, histidine, caffeine, procaine, hydrabamine, choline, imidazole, betaine, ethylenediamine, glucosamine, methylglucamine, theobromine, purines piperazine, N,N-dibenzylethylenediamine, piperidine, N,ethyl-piperidine, morpholine, N-ethylmorpholine, polyamine resins and the like.

Preferred compounds of the present invention comprise the compounds of formula I wherein:

$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) —$(CH_2)_nM$ wherein n is 0 or 1 and M is as defined previously for Formula I;

$R^{11}$ is —$C(O)OR^{19}$; —$C(O)OR^{20}$; $CH_2OH$; CHO; 5-tetrazolyl; —$C(O)NHS(O)_2R^{13}$; or $C(O)CH_2OH$;

r is 1 to 6; and the remaining substituents are as defined previously for Formula I.

More preferred compounds of the present invention comprise the compounds of Formula I. wherein:

A is attached to the 6-or 7- position;

$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) M wherein M is as defined initially for Formula I;

$R^{11}$ is —$CO_2H$; $CH_2OH$; CHO; 5-tetrazolyl or —$C(O)NHS(O)_2R^{13}$;

r is 1 or 2; and the remaining substituents are as defined initially for Formula I.

Most preferred compounds of the present invention comprise the compounds of Formula I. wherein:

A is attached to the 6- or 7-position;

$R^1$, $R^2$, $R^3$ and $R^4$ are each independently selected from:
(1) hydrogen;
(2) alkyl having 1 to 6 carbon atoms;
(3) M wherein M is
  (a) —$C(O)OR^{15}$
  (b) —$C(O)NR^{17}R^{17}$
  (c) —CN;
  (d) —$C(O)R^{16}$
  (f) —$CF_3$;
  (h) -tetrazole;
  (i) —$OR^{12}$;
  (j) —$OC(O)R^{16}$;
  (m) —$SR^{13}$;
  (n) —$S(O)R^{13}$;
  (o) —$S(O)_2R^{13}$;
  (p) —$S(O)_2NR^{17}R^{17}$;
  (t) —$N_3$;
  (v) -halogen;

$R^5$ and $R^6$ are independently selected from:
(1) hydrogen
(2) alkyl having 1 to 6 carbon atoms
(3) M wherein M is
  (a) —$C(O)OR^{15}$
  (b) —$C(O)NR^{17}R^{17}$
  (c) —CN
  (d) —$C(O)R^{16}$
  (f) —$CF_3$
  (h) -tetrazole
  (n) —$S(O)R^{13}$
  (o) —$S(O)_2R^{13}$
  (p) —$S(O)_2NR^{17}R^{17}$
  (t) —$N_3$
  (u) —$NO_2$
  (v) -halogen each $R^{10}$ is independently H, or alkyl of 1 to 4 carbons;

$R^{11}$ is —$CO_2H$; 5-tetrazolyl; or —$C(O)NHS(O)_2R^{13}$;

r is 1 and the remaining substituents are as defined initially for Formula I.

In the above most preferred embodiment, those compounds are particularly preferred wherein at least one of $R^1$ or $R^4$ is not hydrogen; one of $R^5$ or $R^6$ is not hydrogen; $R^7$ is hydrogen; $R^9$ is hydrogen; $R^{16}$ is hydrogen; and the remaining substituents are as defined in the most preferred embodiment.

The novel compounds in Table 1 are a further embodiment of the present invention, and Tables 2–5 show representative starting materials for the preparation of the Formula I compounds.

TABLE 1

Novel Cyclohept[b]indole Alkanoic Acids

| Compound | $R^1$ | $R^2$ | $R^5$ | $R^6$ | $R^7$ | $R^8$ | $(CR^9R^{10})_r$ | $R^{11}$ |
|---|---|---|---|---|---|---|---|---|
| 1 (Ex. 1) | 2-F | H | 4'-Cl | H | H | H | 7-$CH_2$ | $CO_2H$ |
| 2 (Ex. 1) | 2-F | H | 4'-Cl | H | H | H | 10-$CH_2$ | $CO_2H$ |
| 3 (Ex. 2) | 2-F | H | 4'-Cl | H | H | H | r = 0 | 7-$CO_2H$ |
| 4 (Ex. 3) | 2-F | H | 4'-Cl | H | H | H | 6-$CH_2$ | $CO_2H$ |
| 5 | H | H | H | H | H | H | 7-$CH_2$ | $CO_2H$ |
| 6 | H | H | 4'-Cl | H | H | H | 6-$CH_2$ | $CO_2H$ |
| 7 | 2-F | 4-F | 4'-Cl | H | H | H | 7-$CH_2$ | $CO_2H$ |
| 8 | 2-F | 4-F | 4'-Cl | H | H | H | 6-$CH_2$ | $CO_2H$ |
| 9 | 2-F | 4-F | 4'-Cl | H | H | H | r = 0 | 7-$CO_2H$ |
| 10 | 2-OMe | 4-F | 4'-Cl | H | H | H | r = 0 | 6-$CO_2H$ |

TABLE 1-continued
Novel Cyclohept[b]indole Alkanoic Acids

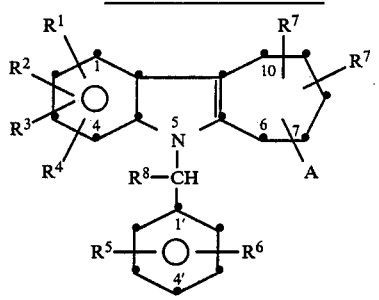

I

| Compound | $R^1$ | $R^2$ | $R^5$ | $R^6$ | $R^7$ | $R^8$ | $(CR^9R^{10})_r$ | $R^{11}$ |
|---|---|---|---|---|---|---|---|---|
| 11 | 4-F | H | 4'-Cl | H | H | H | 7-CH$_2$ | CO$_2$H |
| 12 | 4-F | H | 4'-Cl | H | H | H | 6-CH$_2$ | CO$_2$H |
| 13 | 4-SMe | H | 4'-Cl | H | H | H | r = 0 | 7-CO$_2$H |
| 14 | 4-Ph | H | 4'-Cl | H | H | H | r = 0 | 6-CO$_2$H |
| 15 | 4-Me | H | 4'-Cl | H | H | H | 7-CH$_2$ | CO$_2$H |
| 16 | 4-Me | H | 4'-Cl | H | H | H | 6-CH$_2$ | CO$_2$H |
| 17 | 4-Me | H | 4'-Cl | H | H | H | r = 0 | 7-CO$_2$H |
| 18 | 4-Me | H | 4'-Cl | H | H | H | r = 0 | 6-CO$_2$H |
| 19 | 2-F | 4-F | 2'-Cl | H | H | H | 7-CH$_2$ | CO$_2$H |
| 20 | 2-F | 4-F | 2'-Cl | H | H | H | 6-CH$_2$ | CO$_2$H |
| 21 | 2-F | 4-F | 2'-Cl | H | H | H | r = 0 | 7-CO$_2$ |
| 22 | 2-F | 4-F | 2'-Br | H | H | H | r = 0 | 6-CO$_2$H |
| 23 | 2-F | 4-F | 3'-CF$_3$ | H | H | H | 7-CH$_2$ | CO$_2$H |
| 24 | 2-F | 4-F | 3'-Cl | H | H | H | 6-CH$_2$ | CO$_2$H |
| 25 | 2-F | 4-F | 3'-Cl | H | H | H | r = 0 | 7-CO$_2$H |
| 26 | 2-F | 4-F | 3'-Cl | H | H | H | r = 0 | 6-CO$_2$H |
| 27 | 2-F | 4-F | 2'-Cl | 4'-Cl | H | H | 7-CH$_2$ | CO$_2$H |
| 28 | 2-F | 4-F | 2'-Cl | 4'-Cl | H | H | 6-CH$_2$ | CO$_2$H |
| 29 (Ex. 7) | 2-F | H | 4'-S(O)$_2$Me | H | H | H | 6-CH$_2$ | CO$_2$H |
| 30 | 2-F | 4-F | 2'-Cl | 4'-Cl | H | H | r = 0 | 6-CO$_2$H |
| 31 | 2-F | 4-F | 3'-Cl | 4'-Cl | H | H | 7-CH$_2$ | CO$_2$H |
| 32 | 2-F | 4-F | 3'-Cl | 4'-Cl | H | H | 6-CH$_2$ | CO$_2$H |
| 33 | 2-F | 4-F | 3'-Cl | 4'-Cl | H | H | r = 0 | 7-CO$_2$H |
| 34 | 2-F | 4-F | 3'-Cl | 4'-Cl | H | H | r = 0 | 6-CO$_2$H |
| 35 | 2-F | 4-F | 4'-S(O)$_2$Me | H | H | H | 6-CH$_2$ | CO$_2$H |
| 36 (Ex. 4) | 2-F | 4-F | 4'-S(O)$_2$Me | H | H | H | 7-CH$_2$ | CO$_2$H |
| 37 | 2-F | 4-F | 4'-S(O)$_2$Me | H | H | H | r = 0 | 7-CO$_2$H |
| 38 | 2-F | 4-F | 4'-S(O)$_2$Me | H | H | H | r = 0 | 6-CO$_2$H |
| 39 | 2-F | 4-F | 4'-SMe | H | H | H | 7-CH$_2$ | CO$_2$H |
| 40 | 2-F | 4-F | 4'-SMe | H | H | H | 6-CH$_2$ | CO$_2$H |
| 41 | 2-F | 4-F | 4'-SMe | H | H | H | r = 0 | 7-CO$_2$H |
| 42 | 2-F | 4-F | 4'-SMe | H | H | H | r = 0 | 6-CO$_2$H |
| 43 | 2-F | 4-F | 4'-S(O)Me | H | H | H | 7-CH$_2$ | CO$_2$H |
| 44 | 2-F | 4-F | 4'-S(O)Me | H | H | H | 6-CH$_2$ | CO$_2$H |
| 45 | 2-F | 4-F | 4'-S(O)Me | H | H | H | r = 0 | 7-CO$_2$H |
| 46 | 2-F | 4-F | 4'-S(O)Me | H | H | H | r = 0 | 6-CO$_2$H |
| 47 | 2-F | 4-F | 4'-CF$_3$ | H | H | H | 7-CH$_2$ | CO$_2$H |
| 48 | 2-F | 4-F | 4'-CF$_3$ | H | H | H | 6-CH$_2$ | CO$_2$H |
| 49 | 2-F | 4-F | 4'-CF$_3$ | H | H | H | r = 0 | 7-CO$_2$H |
| 50 | 2-F | 4-F | 4'-CF$_3$ | H | H | H | r = 0 | 6-CO$_2$H |
| 51 | 2-F | 4-F | 4'-F | H | H | H | 7-CH$_2$ | CO$_2$H |
| 52 | 2-F | 4-F | 2'-F | 4'F | H | H | 7-CH$_2$ | CO$_2$H |
| 53 (Ex. 5) | 2-F | 4-F | 4'-C(O)Me | H | H | H | 7-CH$_2$ | CO$_2$H |
| 54 | 2-F | 4-F | 4'-C(O)Me | H | H | H | 7-CH$_2$ | CO$_2$H |
| 55 (Ex. 6) | 2-F | 4-F | 4'-S(O)$_2$NMe$_2$ | H | H | H | 7-CH$_2$ | CO$_2$H |
| 56 | 2-F | 4-F | 3'-S(O)$_2$NMe$_2$ | H | H | H | 6-CH$_2$ | CO$_2$H |
| 57 | 2-F | 4-F | 4'-C(O)NMe$_2$ | H | H | H | 7-CH$_2$ | CO$_2$H |
| 58 | 2-F | 4-F | 4'-C(O)Me | H | H | H | 7-CH$_2$ | CO$_2$H |
| 59 | 2-F | 4-F | 4'-C(O)Me | H | H | H | 7-CH$_2$ | CO$_2$H |
| 60 | 2-F | 4-F | 4'NHC(O)Me | H | H | H | 7-CH$_2$ | CO$_2$H |
| 61 | 2-F | 4-F | 4'NHS(O)$_2$Me | H | H | H | 7-CH$_2$ | CO$_2$H |
| 62 | 2-F | 4-F | 4'NHC(O)NHMe | H | H | H | 6-CH$_2$ | CO$_2$H |
| 63 | 2-F | 4-F | 4'OMe | H | H | H | 7-CH$_2$ | CO$_2$H |
| 64 | 2-F | 4-F | 4'OCH$_2$CO$_2$H | H | H | H | 7-CH$_2$ | CO$_2$H |
| 65 | 2-F | 4-F | 4'-H | H | H | H | 7-CH$_2$ | CO$_2$H |
| 66 | 2-F | 4-F | 4'-Br | H | H | H | 7-CH$_2$ | CO$_2$H |
| 67 | 2-F | 4-F | 4'-Cl | H | H | H | 7-CH$_2$ | CO$_2$H |
| 68 | 2-F | 4-F | 4'-S(O)$_2$Me | H | H | H | 7-CH$_2$ | CH$_2$OH |
| 69 | 2-F | 4-F | 4'-Cl | H | H | H | 7-CH$_2$ | CHO |
| 70 | 2-F | 4-F | 4'-S(O)$_2$Me | H | H | H | 7-CH$_2$ | CHO |
| 71 | 2-F | 4-F | 4'-Cl | H | H | H | 7-CH$_2$ | (Tetrazol-5-yl) |
| 72 | 2-F | 4-F | 4'-S(O)$_2$Me | H | H | H | 7-CH$_2$ | (Tetrazol-5-yl) |
| 73 | 2-F | 4-F | 4'-Cl | H | H | H | 6-CH$_2$ | (Tetrazol-5-yl) |

TABLE 1-continued
Novel Cyclohept[b]indole Alkanoic Acids

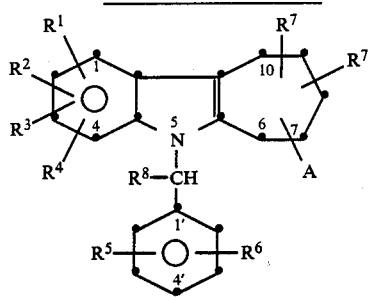

| Compound | $R^1$ | $R^2$ | $R^5$ | $R^6$ | $R^7$ | $R^8$ | $(CR^9R^{10})_r$ | $R^{11}$ |
|---|---|---|---|---|---|---|---|---|
| 74 | 2-F | 4-F | 4'-S(O)$_2$Me | H | H | H | 6-CH$_2$ | (Tetrazol-5-yl) |
| 75 | 2-F | 4-F | 4'-S(O)$_2$Me | H | H | H | r = 0 | 7-(Tetrazol-5-yl) |
| 76 | 2-F | 4-F | 4'-S(O)$_2$Me | H | H | H | r = 0 | 7-(Tetrazol-5-yl) |
| 77 | 2-F | 4-F | 4'-Cl | H | H | H | 7-CH$_2$ | CONHS(O)$_2$Ph |
| 78 | 2-F | 4-F | 4'-S(O)$_2$Me | H | H | H | 7-CH$_2$ | CONH$_2$ |
| 79 | 2-F | 4-F | 4'-Cl | H | H | H | 7-CH$_2$ | NHS(O)$_2$OH |
| 80 | 2-F | 4-F | 4'-C(O)Me | H | H | H | 6-CHMe | CO$_2$H |
| 81 | 2-F | 4-F | 4'-NO$_2$ | H | H | H | 6-CMe$_2$ | CO$_2$H |
| 82 | 2-F | 4-F | 4'-S(O)$_2$NMe$_2$ | H | H | H | 6-(CH$_2$)$_2$ | CO$_2$H |
| 83 | 2-F | 4-F | 4'-Cl | H | H | H | 6-(CH$_2$)$_2$ | CO$_2$H |
| 84 | 2-F | 4-F | 4'-Cl | H | 7-Me | H | 7-CH$_2$ | CO$_2$H |
| 85 | 2-F | 4-F | 4'-Cl | H | 6-Me | H | 7-CH$_2$ | CO$_2$H |
| 86 | 2-F | 4-F | 4'-Cl | H | H | Me | 7-CH$_2$ | CO$_2$H |
| 87 | 2-F | 4-F | 4'-Cl | H | H | H | 8-CH$_2$ | CO$_2$H |
| 88 | 2-F | 4-F | 4'-Cl | H | H | H | 9-CH$_2$ | CO$_2$H |
| 89 | 2-F | 4-F | 4'-Cl | H | H | H | cycloprop-1-yl | CO$_2$H |
| 90 | 2-F | 4-F | 4'-Cl | H | H | H | 7-CH(c-C$_3$H$_5$) | CO$_2$H |
| 91 | 2-SMe | H | 4'-Cl | H | H | H | 7-CH$_2$ | CO$_2$H |
| 92 | 2-S(O)Me | H | 4'-Cl | H | H | H | 7-CH$_2$ | CO$_2$H |
| 93 | 2-S(O)$_2$Me | H | 4'-Cl | H | H | H | 7-CH$_2$ | CO$_2$H |
| 94 isomer (−) | 2-F | 4-F | 4'-S(O)$_2$Me | H | H | H | 7-CH$_2$ | CO$_2$H |
| 95 isomer (+) | 2-F | 4-F | 4'-S(O)$_2$Me | H | H | H | 7-CH$_2$ | CO$_2$H |
| 96 isomer (−) | 2-F | 4-F | 4'-S(O)$_2$Me | H | H | H | 6-CH$_2$ | CO$_2$H |
| 97 isomer (+) | 2-F | 4-F | 4'-S(O)$_2$Me | H | H | H | 6-CH$_2$ | CO$_2$H |

TABLE 2
PhenylHydrazines of Formula IV

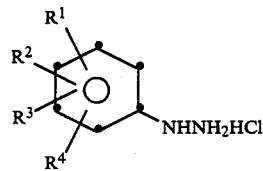

| No. | $R^1$ | $R^2$ | Compound Name |
|---|---|---|---|
| 1 | 4-SMe | H | 4-methylthiophenylhydrazine hydrochloride |
| 2 | 2-CH(Me)$_2$ | H | 2-isopropylphenylhydrazine hydrochloride |
| 3 | 2-SMe | H | 2-methylthiophenylhydrazine hydrochloride |
| 4 | 2-Me | 4-Me | 2,4-dimethylphenylhydrazine hydrochloride |
| 5 | 2-Me | 4-OMe | 4-methoxy-2-methylphenyl-hydrazine hydrochloride |

$R^3 = R^4 = H$

TABLE 3
1-Benzyl Phenylhydrazines of Formula II

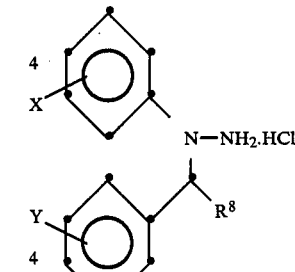

| Compound No. | X | Y | $R^8$ | Compound Name |
|---|---|---|---|---|
| 1. | 4-F | 4-Cl | H | 1-(4-chlorobenzyl)-1-(4-fluorophenyl) hydrazine hydrochloride |
| 2. | 3,5-Cl$_2$ | 4-Cl | H | 1-(4-chlorobenzyl)-1-(3,5-dichlorophenyl)hydrazine hydrochloride |
| 3. | 4-OMe | 4-Cl | H | 1-(4-chlorobenzyl)-1-(4-methoxyphenyl) hydrazine hydrochloride |
| 4. | 2-Me | 4-Cl | H | 1-(4-chlorobenzyl)-1-(2-methoxyphenyl) hydrazine |

TABLE 3-continued
1-Benzyl Phenylhydrazines of Formula II

| Compound No. | X | Y | $R^8$ | Compound Name |
|---|---|---|---|---|
| 4. | 2-Me | 4-Cl | H | 1-(4-chlorobenzyl)-1-(2-methylphenyl) hydrazine hydrochloride |
| 5. | 4-Me | 4-Cl | H | 1-(4-chlorobenzyl)-1-(4-methylphenyl) hydrazine hydrochloride |
| 6. | 4-Cl | 4-Cl | H | 1-(4-chlorobenzyl)-1-(4-chlorophenyl) hydrazine hydrochloride |
| 7. | H | 4-Cl | H | 1-(4-chlorobenzyl)-1-(phenyl) hydrazine hydrochloride |
| 8. | 4-Br | 4-Cl | H | 1-(4-chlorobenzyl)-1-(4-bromophenyl) hydrazine hydrochloride |
| 9. | 3-F | 4-Cl | H | 1-(4-chlorobenzyl)-1-(3-fluorophenyl) hydrazine hydrochloride |
| 10. | 2,4-Cl$_2$ | 4-Cl | H | 1-(4-chlorobenzyl)-1-(2,4-dichlorophenyl)hydrazine hydrochloride |
| 11. | 4-F | H | H | 1-(benzyl)-1-(4-fluorophenyl) hydrazine hydrochloride |
| 12. | 4-F | 4-OMe | H | 1-(4-methoxybenzyl)-1-(4-fluorophenyl) hydrazine hydrochloride |
| 13. | 4-F | 3,4-Cl$_2$ | H | 1-(3,4-dichlorobenzyl)-1-(4-fluoro-phenyl) hydrazine hydrochloride. |
| 14. | 4-F | H | CH$_3$ | 1-[1-(phenyl)ethyl]-1-(4-fluorophenyl) hydrazine hydrochloride |
| 15. | 2-F | 4-Cl | H | 1-(4-chlorobenzyl)-1-(2-fluorophenyl) hydrazine hydrochloride. |
| 16. | 4-CH(Me)$_2$ | 4-Cl | H | 1-(4-chlorobenzyl)-1-(4-isopropylphenyl)hydrazine hydrochloride |
| 17. | 4-C(Me)$_3$ | 4-Cl | H | 1-(4-chlorobenzyl)-1-(4-tert-butylphenyl)hydrazine)hydrochloride |
| 18. | 4-CF$_3$ | 4-Cl | H | 1-(4-chlorobenzyl)-1-(4-trifluoromethylphenyl)-hydrazine hydrochloride |
| 19. | 4-SMe | 4-Cl | H | 1-(4-chlorobenzyl)-1-(4-methylthiophenyl)hydrazine hydrochloride |
| 20. | 2-CH(Me)$_2$ | 4-Cl | H | 1-(4-chlorobenzyl)-1-(2-isopropylphenyl)hydrazine hydrochloride |

The following ketones are known in the art.

TABLE 4
Ketones of Formula III

| No. | Structure | References |
|---|---|---|
| 1. | (3-oxocycloheptane structure with $CO_2H$) | 3-Oxocycloheptaneacetic acid; Chem. Ber., 102, 3877 (1969); M. Regitz and J. Ruter |
| 2. | (3-oxocycloheptane structure with CN) | 3-Oxocycloheptane carbonitrile Tetrahedron, 28, 4051 (1977); H. Newman and T. L. Fields |
| 3. | (oxocycloheptane structure with $CO_2Et$) | Ethyl 2-oxocycloheptane acetate J. Chem. Soc., Perkin Trans 1,2485 (1975); I. W. Sinclair and E. R. Proctor |

TABLE 5
Benzyl Halides of Formula V

| Compound No. | Z | $R^5$ | $R^6$ | Compound Name |
|---|---|---|---|---|
| 1. | Cl | 4-Cl | H | 4-chlorobenzyl chloride (ALDRICH) |
| 2. | Cl | 4-OMe | H | 4-methoxybenzyl chloride (ALDRICH) |
| 3. | Cl | 2-Cl | 4-Cl | 2,4-dichlorobenzyl chloride (ALDRICH) |
| 4. | Br | 2-Cl | H | 2-chlorobenzyl bromide (ALDRICH) |
| 5. | Br | 3-Cl | H | 3-chlorobenzyl bromide (ALDRICH) |
| 6. | Br | 4-F | H | 4-fluorobenzyl bromide (ALDRICH) |
| 7. | Br | 4-CF$_3$ | H | 4-trifluoromethylbenzyl bromide (ALDRICH) |
| 8. | Cl | 4-CO$_2$Me | H | 4-carbomethoxybenzyl chloride (J.A.C.S. 1950, 72, 5152) |
| 9. | Cl | 4-SMe | H | 4-methylthiobenzyl chloride (C.A.:56:4773 (1962)) |
| 10. | Cl | 4-SOMe | H | 4-methylsulfinylbenzyl chloride (C.A.:84:105277h (1976)) |
| 11. | Cl | 4-SO$_2$Me | H | 4-methylsulfonylbenzyl chloride (C.A.:78:111325q (1973)) |
| 12. | Br | 4-NO$_2$ | H | 4-nitrobenzyl bromide (ALDRICH) |
| 13. | Cl | 4-CONMe$_2$ | H | 4-dimethylcarboxamidobenzyl chloride |
| 14. | Cl | 4-SO$_2$NMe$_2$ | H | 4-dimethylsulfamoylbenzyl chloride C.A. 84:135484r (1976) |

TABLE 5-continued

Benzyl Halides of Formula V

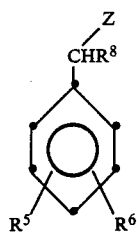

| Compound No. | Z | R⁵ | R⁶ | Compound Name |
|---|---|---|---|---|
| 15. | Cl | 4-CO₂H | H | 4-carboxybenzyl chloride (ALDRICH) |
| 16. | Cl | 4-COMe | H | 4-acetylbenzyl chloride (C.A.:93:239994; (1980)) |

The following reaction schemes illustrate the preparation of the compounds of the present invention:

Scheme 1 Preparation of Formula I Compounds

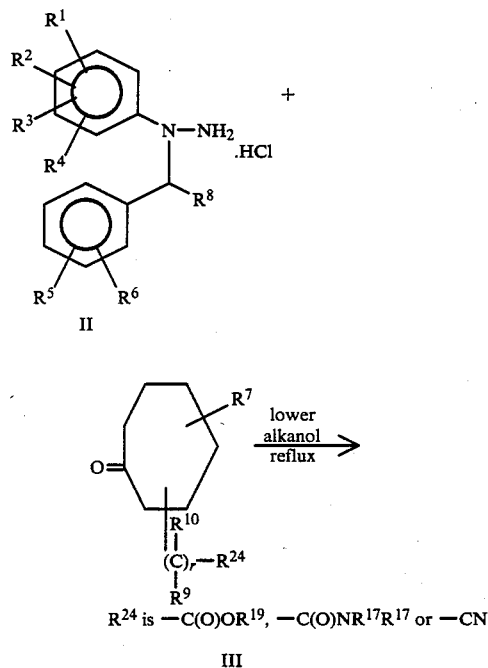

$R^{24}$ is $-C(O)OR^{19}$, $-C(O)NR^{17}R^{17}$ or $-CN$

III

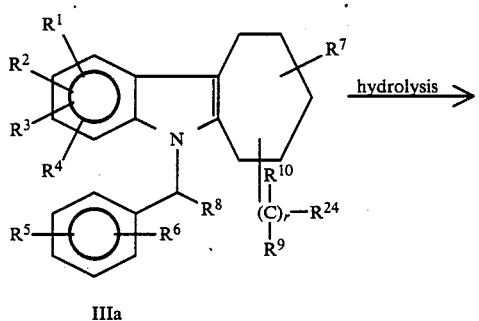

IIIa

-continued
Scheme 1 Preparation of Formula I Compounds

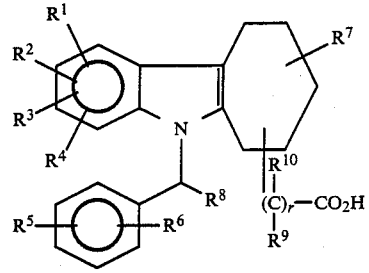

Ib (IIIa is Ia when $R^{24}$ is $-C(O)OR^{19}$ or $-C(O)NR^{17}R^{17}$)

Compound IIIa (Scheme I) is prepared using standard Fisher Indole conditions (See, for example, the review in "Heterocyclic compounds", 25 Parts I, II and III, W. J. Houlihan, ed, Interscience, John Wiley & Sons, New York, 1979).

Thus, treatment of the phenylhydrazine II with the ketone III is an alcoholic solvent at a temperature between 20° C. and the refluxing temperature of the solvent yields IIIa (or Ib when $R^{24}$ is CO₂H. Illustrative of such alcoholic solvent are: methanol, ethanol, isopropanol, tert-butanol, tert, amylalcohol and the like.

Hydrolysis of IIIa is conveniently carried out by using NaOH, KOH, LiOH or Ba(OH)₂ in solutions of aqueous ethanol, methanol or tetrahydrofuran or mixtures thereof, followed by acidification to obtain compounds of Formula Ib.

Scheme II Preparation of 1-Benzyl Phenylhydrazines (II)

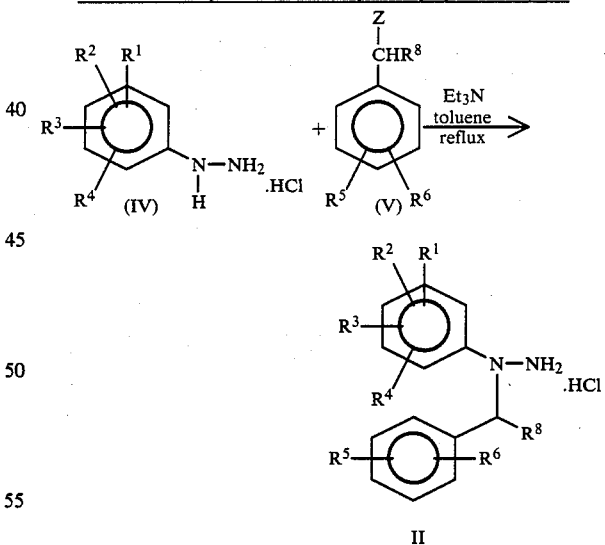

II

Z is a leaving group such as Cl, Br, I, mesylate or tosylate

With regard to Scheme II, the preparation of the 1-benzyl phenylhydrazine starting materials is illustrated by the preparation of 1-(4-chlorobenzyl)-1-(4-methoxyphenyl)hydrazine. A mixture of 10 g of p-methoxyphenylhydrazine hydrochloride, 75 ml of toluene and 11.5 ml of triethylamine was heated at reflux for 60 minutes. Then, 7.1 g of p-chlorobenzyl chloride was added. After stirring 16 hours at reflux, triethylamine hydrochloride was filtered off and washed with ethyl ether. The filtrate and washing were concentrated in vacuo and chromatographed on a silica gel column (hexane-ethyl acetate, 9:1) to give 6.64 g of 1-(4-chlorobenzyl)-1-(4-methoxyphenyl)hydrazine. Other hydrazines, similarly prepared, are also shown in Table 3.

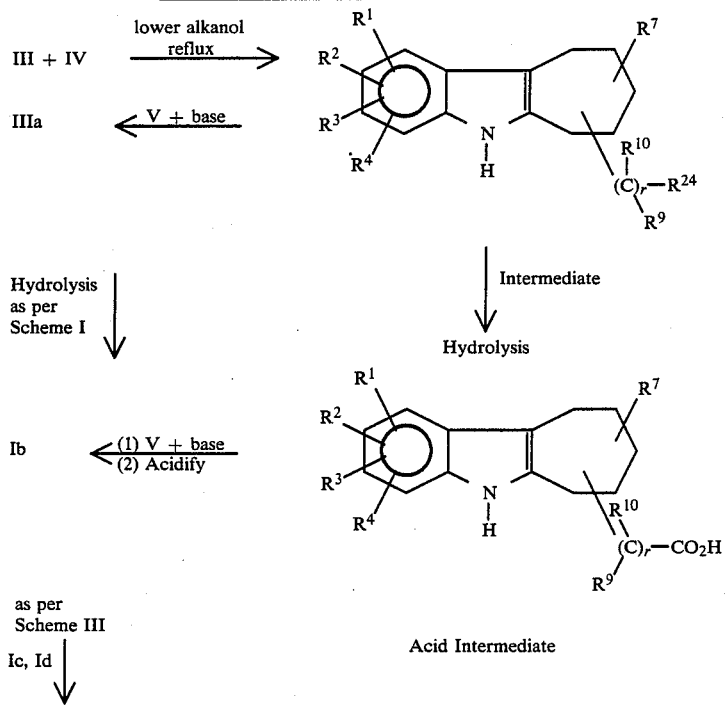

Ogliaruso and Wolfe in Patai, *The Chemistry of Acid Derivatives*, Supplement B, Wiley, New York, 1979, pp. 411-436) which is hereby incorporated br reference.

Scheme IV illustrates alternative syntheses of the compounds of Formula I. In this Scheme a Fischer indole synthesis is carried out using a phenylhydrazine IV and the ketone III, followed by hydrolysis. The acid intermediate is then N-benzylated with the reagent V, preferably using a strong base such as potassium t-butoxide, ethyl magnesium bromide (EtMgBr), lithium diisopropylamide (LDA), potassium hydride (KH), sodium hydride (NaH) or potassium hexamethyldisilazide (KHMDS) to effect the reaction. Acidification of the reaction mixture then yields the free acid Ib which can be converted to compounds of Formulae Ic or Id as indicated in Scheme III. Alternatively, the Intermediate

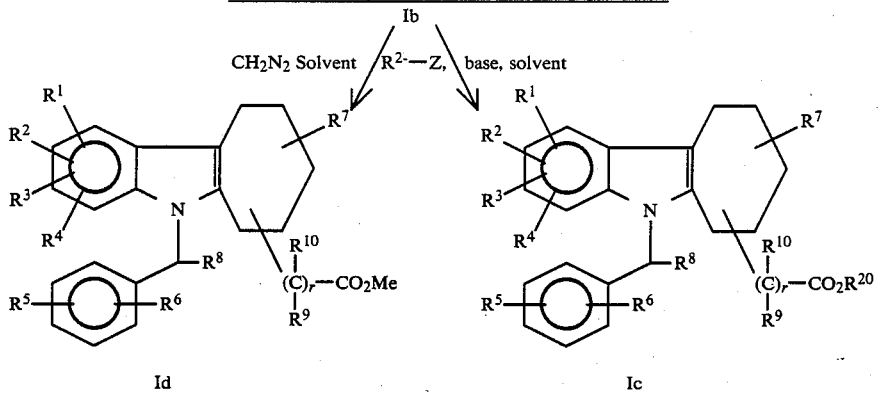

To prepare certain esters representative of the Formula I compounds, it may be advantageous to first prepare the carboxylic acids Ib as illustrated in Scheme I. The carboxylic acid is then reacted, as shown in Scheme III, with an alkylating agent, $R^{20}$-Z, in the presence of a suitable base and solvent combination, such as for example, $Na_2CO_3$ in acetone or triethylamine in dimethylformamide, to produce the esters Ic.

Another method of preparing the esters of Formula I from the acid consists of treating the latter with a diazoalkane (such as diazomethane) in a suitable non-reactive solvent such as ether or methanol to obtain an ester Id. Other methods of esterification are shown in can be N-benzylated to IIIa, which is then convertible to Ib as per Scheme I.

Compound Ie (a representative of Ia, Ib, Ic or Id) is prepared according to Scheme I or Scheme III. Treatment of Ie with a limited amount of an oxidizing agent such as m-chloroperbenzoic acid yields the sulfoxide If, which upon hydrolysis (if necessary) yields sulfoxide acid Ig. Further treatment of If with the oxidizing agent, or treatment of Ie with an excess (>2 eq.) of the oxidizing agent yields the sulfone Ih, hydrolysis (if necessary) of which yields the sulfone acid Ii.

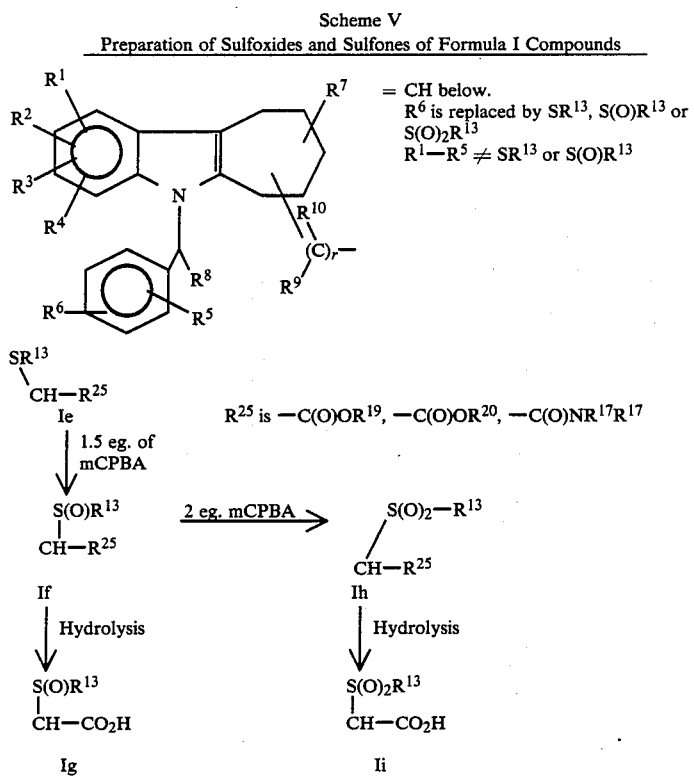

In Scheme V is illustrated a method of preparing derivatives of Formula I in which one of the substituents ($R^6$) is a sulfoxide or a sulfone. It will be obvious to one skilled in the art that a sulfoxide or sulfone derivative of $R^1$-$R^4$ could be prepared in the same way.

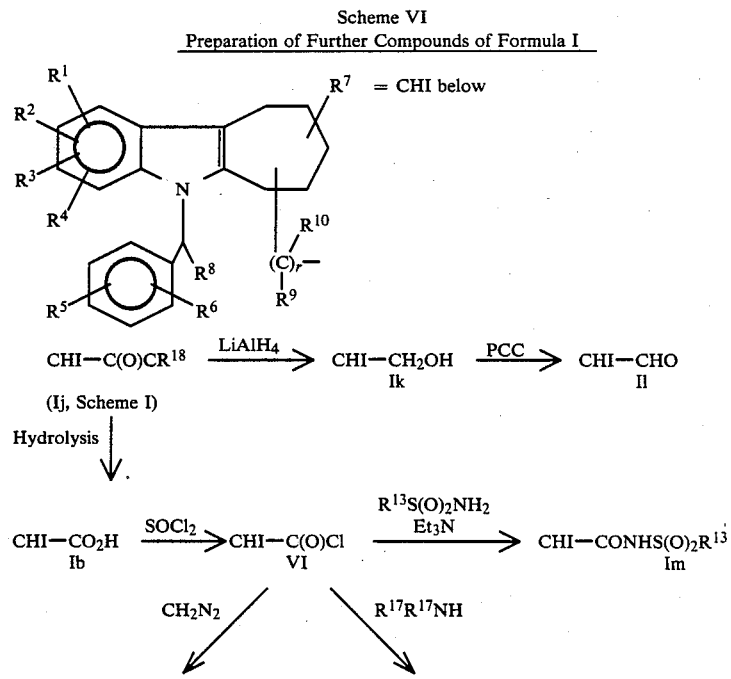

Scheme VI
Preparation of Further Compounds of Formula I

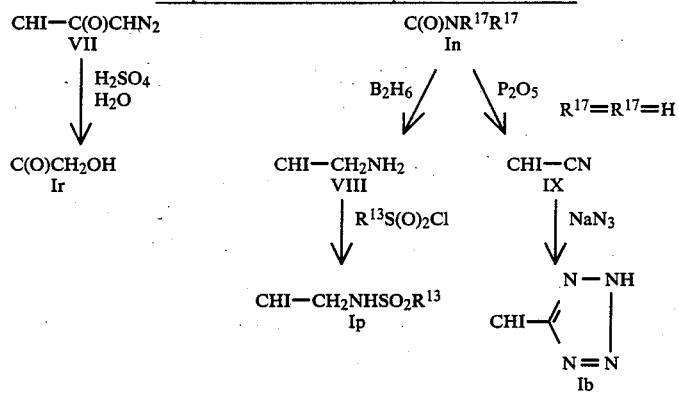

Other compounds of Formula I can be prepared as indicated in Scheme VI. Thus the ester derivative Ij can be reduced to the alcohol Ik by lithium aluminum hydride or other suitable reducing agents. Alcohol Ik can then be oxidized to aldehyde Il by pyridinium chlorochromate or other suitable oxidizing agents. Carboxylic acids of Formula Ib can be converted to the acid chloride VI (the acid bromide or a mixed carbonate anhydride could also be used) which when reacted with diazomethane yields the diazoketone VII. Compound VII, upon reaction with aqueous acid, preferably a nonnucleophilic acid such as sulfuric acid or p-toluenesulfonic acid, is converted to the hydroxymethyl ketone Ir.

Acid chloride VI, upon reaction with a sulfonamide, $R^{13}S(O)_2NH_2$, in the presence of a weak base yields the acylsulfonamide Im. Reaction of VI with an amine, $R^{17}R^{17}NH$, yields amide In. Amide In can be sequentially reduced, to amine VIII, with diborane or lithium aluminum hydride, and sulfonylated with $R^{13}S(O)_2Cl$ to produce sulfonamide Io. Amide In (when both $R^{17}$ substituents are hydrogen) can be dehydrated by standard reagents to nitrile IX, which is converted to tetrazole Iq by reaction with sodium azide, tri-n-butyltin azide or other suitable methods.

Scheme VII
Preparation of Phenylhydrazines IV

R¹, R², R³, R⁴-substituted-NH₂·HCl
(1) NaNO₂
(2) Na₂S₂O₄
→
R¹, R², R³, R⁴-substituted-NHNH₂·HCl

IV

With regard to Scheme VII, the preparation of hydrazine starting materials is illustrated by preparation of 4-methylthiophenyl hydrazine hydrochloride. 4-Methylthioaniline (13.9 g) was added dropwise to cold HCl (6N) (50 mL) and stirred for 5 min in an ice bath. A solution of NaNO₂ in water (7.25 g, 15 mL) was then added dropwise and stirred for 15 min. The cold diazonium salt was then cannulated into a stirred cold solution of $Na_2S_2O_4$ in water (50 g, 250 mL). After 20 min, ether (200 mL) was added and the reaction mixture basified with NaOH(10N). The ether layer was decanted, washed with brine, dried over $Na_2SO_4$ and HCl gas was passed through the ether solution to form the hydrochloride salt which precipitated out. After filtration, there was obtained 7.0 g of pure final product. Other hydrazines, similarly prepared, are also shown in Table 2.

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

The prostaglandin antagonist properties of the compounds of the present invention can be demonstrated by a number of biological assays, two of which, inhibition of platelet aggregation and measurement of $pA_2$ valves are described below.

Inhibition of Induced Threshold Aggregation of Human Platelets

Human platelet rich plasma (PRP) is prepared from venous blood of male volunteers who have taken no medication for ten days prior to test. Blood is transferred into plastic centrifuge tubes containing 3.8% Trisodium Citrate in 0.9% NaCl (in a ratio of blood to anticoagulant of 9:1), mixed by gentle inversion, and centrifuged at room temperature for ten minutes at 116 g. The supernatant (PRP) is transferred into plastic tubes. Platelet poor plasma (PPP) is obtained by centrifuging the residual blood cells at 4000 g for ten minutes. PRP is left to stand at least one half hour prior to testing.

Platelet aggregation is measured using a Payton Aggregometer and Recorder. Following calibration of the instrument, a cuvette containing PRP (225 microliters) is incubated for three minutes at 37° C. Drug vehicle (control), or a drug concentration is then added in a volume of 0.5 microliter. After one minute, the aggregating agent (U44069, 9,11-dideoxy-9a,11a-epoxymethano $PGF_{2a}$) is added to the cuvette in a volume of 25 microliters. Recording is continued until the maximal response is obtained.

The threshold (approximately 20-30% of maximum) aggregation concentration of the agonist to be used is first determined in the presence of the drug vehicle (control). Test compounds are then assayed at 10 or 30 micrograms/ml initially, and if active, are further tested in order to determine the concentration range at which 20-80% of the threshold aggregatory response is inhibited. All drugs are dissolved in dimethylsulfoxide.

The height of the aggregation response (measured in divisions of the recorder paper, 1 division=2.5 mm) in the presence of the drug is recorded, and calculated as percent inhibition of the mean height of the control threshold responses. The $IC_{50}$ (drug concentration which inhibits 50 % of the aggregatory response) is obtained by regression analysis.

Estimation of $pA_2$ Values in Guinea Pig Tracheal Chain

Male albino Hartley strain guinea pigs (300-350 gm) were sacrificed by a blow to the head and exsanguinated. The trachea was removed, freed of extraneous tissue and sectioned into rings of 1-2 mm thickness. Five rings were tied together in series, ensuring that the tracheal muscle lay in the same vertical plane, and the cartilage of each ring then separated at a point directly opposite the muscle. The chains were suspended under 1 gm resting tension in modified Krebs solution (NaCl, 6.87; $NaHCO_3$, 2.1; dextrose, 2.1; KCl, 0.32; $CaCl_2$, 0.28; $MgSO_4$, $7H_2O$, 0.11; $KH_2PO_4$, 0.16; gm/L: equilibrated with 5% $CO_2$ in $O_2$ for 1 hour) containing indomethacin ($1.4 \times 1^{-5}M$) to suppress endogenous prostaglandin synthesis, Organ bath temperature was maintained at 37° C. and 5% $CO_2$ in $O_2$ diffused continuously. Isometric tension changes were recorded from a Gould-Statham (UTC 2) force displacement transducer connected to a Beckman Type R Dynograph. For assay purposes initial maximal contractions were elicited with a high concentration of the contractile agonist [U-44069, 9.11-dideoxy-9a, 11a-epoxymethano $PGF_{2a}$] and the tissue subsequently washed at intervals until tension returned to baseline. Agonist dose response curves were obtained using a cumulative-dose schedule (4-8 doses) and the preparations then washed at regular intervals until baseline tension was recorded. After an appropriate interval (1-1.5 hrs) agonist dose response curves were repeated in the presence of antagonist drug concentrations. Drug doses were delivered in 10 ml volumes 5 minutes prior to the second agonist challenge, and cumulative agonist volumes did not exceed 100 ml per bath. $EC_{50}$ values were obtained by regression analysis and used to calculate 'apparent' and Schild Plot $pA_2$ values by the method of Tallarida and Murray 1981.

Compounds of Formula I can be tested using the following assay to determine their mammalian leukotriene biosynthesis inhibiting activity.

Rat Peritoneal Polymorphonuclear (PMN) Leukocyte Assay

Rats under ether anesthesia are injected (i.p.) with 8 ml of a suspension of sodium caseinate (6 grams in ca. 50 ml water). After 15-24 hr. the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted (350× g, 5 min.), resuspended in buffer with vigorous shaking, filtered, through lens paper, recentrifuged and finally suspended in buffer at a concentration of 10 cells/ml. A 500 ml aliquot of PMN suspension and test compound are preincubated for 2 minutes at 37° C., followed by the addition of 10 mM A-23187. The suspension is stirred for an additional 4 minutes then bioassayed for $LTB_4$ content by adding an aliquot to a second 500 ml portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

In Table 6 below are presented data indicating the prostanoid antagonist activities of compounds of the present invention indicated in Table 1. It is to be noted that $pA_2$ values are on a logarithmic scale, so that, for instance, a difference between two $pA_2$ values of 1 represents a difference in potency by a factor of 10.

Compounds A and B in Table 4 are known in the art: U.S. Pat. No. 3,896,145 describes compounds A and U.S. Pat. No. 3,868,387 describes compound B.

Compound A, which is a six-membered ring analog of the novel compound 1, is seventy times less potent than compound 1 as an inhibitor of platelet aggregation. Furthermore, the $PA_2$ of compound A is 1.7 log units lower than that of compound 1 (a factor of 15). Compound B, which is a six-membered ring analog of the novel compound 3, is at least four times less potent than the latter as an inhibitor of platelet aggregation, and has a slightly lower $pA_2$ value. The data of Table 6 also indicates the flexibility of the positioning of the alkanoic acid side chain on the seven-membered ring (compounds 1, 2 and 4).

TABLE 6
Prostanoid Antagonist Activities
| Compound | Inhibition of platelet aggregation (IC$_{50}$ in mg/ml) | pA$_2$ |
|---|---|---|
| A 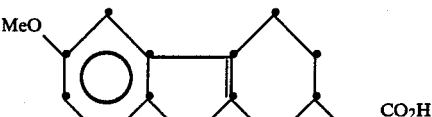 | 3.5 | 6.8 |
| B 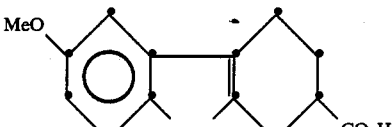 | >30 | 6.8 |
| 1 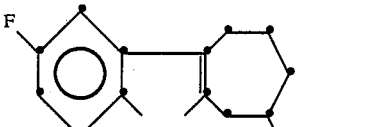 | 0.05 | 8.5 |
| 2 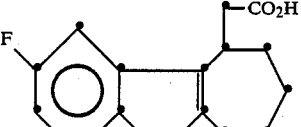 | 4.5 | 7.37 |

TABLE 6-continued

Prostanoid Antagonist Activities

| Compound | Inhibition of platelet aggregation (IC$_{50}$ in mg/ml) | pA$_2$ |
|---|---|---|
| 3 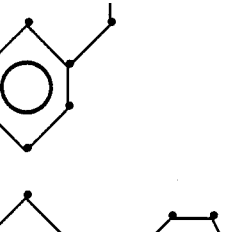 | 7.46 | 6.89 |
| 4 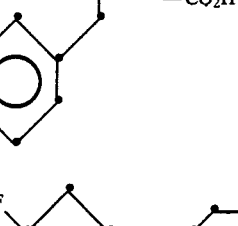 | 0.015 | 8.87 |
| 36 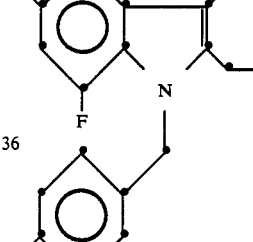 | 0.012 | 8.08 |

The magnitude of a prophylactic or therapeutic dose of a compound of Formula I will, of course, vary with the nature or the severity of the condition to be treated and with the particular compound of Formula I and its route of administration. In general, the daily dose range for anti-asthmatic, anti-allergic, anti-thrombotic or anti-nephrotoxic use lies within the range of from about 0.01 mg to about 100 mg per kg body weight of a mammal.

The exact amount of a compound of Formula I to be used as a cytoprotective agent will depend on, inter alia, whether it is being administered to heal damaged cells or to avoid future damage, on the nature of the damaged cells (e.g., gastro-intestinal ulcerations vs. nephrotic necrosis), and on the nature of the causative agent. An example of use of a compound of Formula I to avoid future damage is coadministration with a non-steroidal anti-inflammatory drug (for example, indomethacin).

The effective daily dosage level for compounds of Formula I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Any suitable route of administration may be employed for providing a mammal, especially a human with an effective dosage of a compound of Formula I. For example, oral, rectal, topical, parenteral, ocular, nasal, buccal, intravenous and the like may be employed. Dosage forms include tablets, troches, dispersions, suspensions, solutions, capsules, creams, ointments, aerosols and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-allergic or anti-nephrotoxic use is from about 0.01 mg to about 20 mg (preferably from about 0.1 mg to about 10 mg) of a compound of Formula I per kg of body weight per day and for cytoprotective use from about 0.002 mg to about 100 mg (preferably from about 0.02 mg to about 30 mg and more preferably from about 0.1 mg to about 10 mg) of a compound of Formula I per kg of body weight per day. In the case where an oral composition is employed, a suitable dosage range for anti-asthmatic, anti-allergic, or anti-nephrotoxic use is, e.g. from about 1 to about 100 mg of a compound of Formula I per kg of body weight per day, preferably from about 5 mg to about 40 per kg and for cytoprotective use from about 0.01 mg to about 100 mg (preferably from about 0.1 mg to about 30 mg and were preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser, or a powder which may be formulated as a cartridge from which the powder composition may be inhaled with the aid of a suitable device. The preferred delivery system for inhalation is a metered dose inhalation (MDI) aerosol, which may be formulated as a suspension or solution in fluorocarbon propellants.

Suitable topical formulations of compound I include transdermal devices, aerosols, creams, ointments, lotions, dusting powder, and the like.

In practical use, a compound of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 2.0 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25.0 |
| Microcrystalline Cellulose | 415.0 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25.0 |
| Lactose Powder | 573.5 |
| Magnesium Stearate | 1.5 |
| | 600 |

In addition to the compounds of Formula I, the pharmaceutical compositions of the present invention can also contain other active ingredients, such as non-steroidal anti-inflammatory drugs (NSAIDs), peripheral analgesic agents such as zomepirac, diflunisal and the like, cyclooxygenase inhibitors, leukotriene antagonists, leukotriene biosynthesis inhibitors, $H_2$-receptor antagonists, antihistaminic agents, prostaglandin antagonists, ACE inhibitors, and thromboxane synthetase inhibitors. The weight ratio of the compound of the Formula I to the second active ingredient may be varied and will depend upon the effective dose of each ingredient. Generally, an effective dose of each will be used. Thus, for example, when a compound of the Formula I is combined with a second active ingredient the weight ratio of the compound of the Formula I to the second ingredient will generally range from about 1000:1 to about 1:1000, preferably from 200:1 to 1:200. Combinations of a compound of the Formula I and other active ingredients will generally be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof. NSAIDs which are within the scope of this invention are those disclosed in EP No. 140,684.

Pharmaceutical compositions comprising the Formula I compounds may also contain other inhibitors of the biosynthesis of the leukotrienes such as are disclosed in EP No. 138,481 (Apr. 24, 1985), EP No. 115,394 (Aug. 8, 1984), EP No. 136,893 (Apr. 10, 1985), and EP No. 140,709 (May 8, 1985), which are hereby incorporated herein by reference.

The compounds of the Formula I may also be used in combination with leukotriene antagonists such as those disclosed in EP No. 106,565 (Apr. 25, 1984) and EP No. 104,885 (Apr. 4, 1984), which are hereby incorporated herein by reference and others known in the art such as those disclosed in European patent application Nos. 56,172 and 61,800; and in U.K. patent specification No. 2,058,785, which are hereby incorporated herein by reference.

Pharmaceutical compositions comprising the Formula I compounds may also contain as the second active ingredient, other prostaglandin antagonists such as those disclosed in European patent application No. 11,067 (May 28, 1980) or other thromboxane antagonists such as those disclosed in U.S. Pat. No. 4,237,160. They may also contain histidine decarboxyase inhibitors such as a-fluoromethyl-histidine, described in U.S. Pat. No. 4,325,961. The compounds of the Formula I may also be advantageously combined with an $H_1$ or $H_2$-receptor antagonist, such as for instance benadryl, dramamine, histadyl, phenergan, terfenadine, acetamazole, cimetidine, ranitidine, famotidine, aminothiadiazoles disclosed in EP 40,696 (Dec. 2, 1981) and like compounds, such as those disclosed in U.S. Pat. Nos. 4,283,408; 4,362,736; 4,394,508; and a pending application, U.S. Ser. No. 301,616, filed Sept. 14, 1981. The pharmaceutical compositions may also contain a $K^+/H^+$ ATPase inhibitor such as omeprazole, disclosed in U.S. Pat. No. 4,255,431, and the like. Compounds of I may also be usefully combined with most cell stabilizing agents, such as 1,3-bis(2-carboxychromon-5-yloxy)-2-hydroxypropane and related compounds described in British patent specification Nos. 1,144,905 and 1,144,906. Another useful pharmaceutical composition comprises the Formula I compounds in combination with serotonin antagonists such as methysergide, the serotonin antagonists described in *Nature*, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

When the second active ingredient in compositions of this invention is a thromboxane synthetase inhibitor, such inhibitor can be as described in UK No. 2,038,821 (e.g., UK No. 37248 and dazoxiben hydrochloride), U.S. Pat. No. 4,217,357 (e.g., UK No. 34787), U.S. Pat. No. 4,444,775 (e.g., CGS 13080), U.S. Pat. No. 4,226,878 (e.g., ONO 046), U.S. Pat. No. 4,495,357 (e.g., U63557A) U.S. Pat. No. 4,273,782 (e.g., UK-38485), or EP No. 98,690 (e.g., CV-4151).

An embodiment of the invention is a cardiovascular composition useful for treating arterial thrombosis which comprises an antithrombotic compound of the Formula I.

A further embodiment of the invention is a cardiovascular composition useful for treating arterial thrombosis which comprises: (1) the antithrombotic Formula I compound defined above; and, (ii) an angiotensin converting enzyme (ACE) inhibitor compound which is a member of the group: carboxyalkyl dipeptide derivatives; captopril [1-(3-mercapto-2-methyl-1-oxopropyl)-L-proline]; 2-[N-(S)-1-ethoxycarbonyl- 3-phenyl-propyl]-S-alanyl]-cis,endo-2-azabicyclo[3,3,0]octane-3(S)-carboxylic acid; N-((S)-1-ethoxycarbonyl-3-phenylpropyl)-L-alanyl-N-(2-indanyl)-glycine; 1-(N-[(S)-1-ethoxy-carbonyl-3-phenylpropyl]-L-alanyl]-cis,-syn-octahydro-(H-indole-2-S)-carboxylic acid; 2-(N-[(S)-1-ethoxy-carbonyl-3-phenylpropyl]-L-alanyl)-1,2,3,4-tetrahydro-iso-isoquinoline-3(S)-carboxylic acid; and, 1-carboxy-methyl-3(S)-(1(S)-ethoxycarbonyl-3-phenylpropylamino)-2,3,4,5-tetrahydro-1H[1]-benzazepine-2-one.

In particular the class of ACE inhibitors which have been found to have a potentiating effect when used in combination with the Formula I compounds are those disclosed in U.S. Pat. No. 4,374,829, which also discloses methods for their preparation and which patent is incorporated herein by reference. Of the carboxyalkyl dipeptides disclosed in U.S. Pat. No. 4,374,829, those of particular interest in this invention are N-[1(S)-ethoxycarbonyl-3-phenylpropyl]-L-alanyl-L-proline, also known and referred to herein as enalapril; N-[1(S)-carboxy-3-phenylpropyl]-L-alanyl-L-proline, also know and referred to herein as enalapril diacid; and, Na-[1(S)-carboxy-3-phenylpropyl]-L-lysyl-L-proline, also known and referred to herein as lisinapril.

The combination composition of the invention can contain varying amounts of (i) the Formula I antithrombotic compound and (ii) ACE inhibitor antihypertensive compounds. The weight ratio of (i):(ii) can range from about 25 to 1; preferably from about 10 to 1. In addition to the active ingredients of (i) alone or of (i) and (ii) in combination, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the present composition.

The combination compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration. These compositions ar formulated similarly to the compositions discussed above.

Treatment dosage for human beings for cardiovascular use can be varied as necessary. Generally, daily dosages of the composition of the invention can range from about 6000 to about 10 mg; preferably, from about 3000 to about 20 mg.

The amount of active ingredient that may be combined with the carrier materials to produce a single dosage form for cardiovascular use will vary depending upon the host treated and the particular mode of administration. For example, a formulation intended for oral administration may contain from 5 mg to 5 gm of active agents compounded with an appropriate and convenient amount of carrier material which may vary from about 5 to about 95 percent of the total composition. Dosage unit forms will generally contain between from about 20 mg to about 500 mg of active ingredients.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The composition of this invention inhibits platelet accumulation at the damaged endothelial surface via the Formula I compound. This inhibitory effect is potentiated by the presence of the antihypertensive compound.

Thus, the compositions of the invention are useful in treating thrombosis and are also of value in the management of acute and chronic congestive heart failure, and limitation of myocardial infarct damage.

In vivo testing of the composition of this invention in test animals (rabbits) can be used to demonstrate that this composition is pharmaceutically effective in decreasing platelet-related arterial thrombic formation.

To demonstrate the potentiation of the antihypertensive compound on the anti-thrombotic Formula I compound comprising the combination composition of the invention, the effect of these compounds on test animals (rabbits) can be determined separately and then in combination. The effect of a different class of antihypertensive agents singly and in combination with the Formula I compound of the invention can also be determined for comparative purposes. The methods employed are described in U.S. Pat. No. 4,558,037 which is hereby incorporated herein by reference.

The following examples illustrate the preparation of the compounds of the present invention without, however, limiting the same thereto.

All temperatures are in degrees Celsius.

EXAMPLE 1

2-Fluoro-5-(p-chlorobenzyl)-5,6,7,8,9,10-hexahydrocyclohept[b]indole-7-acetic acid and 2-Fluoro-5-(p-chlorobenzyl)-5,6,7,8,9,10-hexahydrocyclohept[b]indole-10-acetic acid To 1.10 g of 3-oxo-cycloheptaneacetic acid in 35 mL tert-butanol was added 2.13 g of 1-(p-chlorobenzyl)-1-(p-fluorophenyl) hydrazine hydrochloride, The reaction mixture was refluxed under nitrogen for 18 h, cooled to room temperature and then evaporated to dryness. The resultant residue was partitioned between water and ethyl acetate. The organic layer was washed with 1N HCl (2X), water (2X) and brine and dried over MgSO$_4$. Filtration and concentration gave oil which was purified by flash chromatography on silica gel. Elution of the column with a mixture of hexane-ethyl acetate (7:3) gave the title compound substituted at the 10-position, mp 138°–139° C. IR (KBr) 1703 cm$^{-1}$. 'H NMR (CDCl$_3$, 250 MHz) w 1.32–1.54 (m, 1H), 2.60–2.87 (m, 2H), 2.65 (d, J=7.5 Hz, 2H), 3.72–3.83 (m, 1H), 5.25 (s, 2H), 6.78–6.88 (m, 1H), 6.81 (d, J=8.0 Hz, 2H), 7.04 (d,d, J=4.5, 9.0 Hz, 1H), 7.20–7.30 (buried m, 1H), 7.23 (d, J=8.0 Hz, 2H).

Further elution of the column gave the title compound substituted at the 7-position, mp 141°–142° C. IR (KBr) 1703 CM$^{-1}$. 'H NMR (CDCl$_3$, 250 MHz)w 1.64–1.83 (m, 2 H), 1.85–2.14 (m, 2H), 2.15–2.40 (m, 3H), 2.64–2.95 (m, 4H), 5.24 (s, 2H), 6.78–6.90 (m, 1H), 6.85 (d, J=8.0 Hz, 2H), 7.06 (d,d, J=4.5, 9.0 Hz, 1H), 7.16 (d,d, J=2.5, 10.0 hZ, 1H), 7.21 (d, J=8.0 Hz 2H).

Analysis calculated for C$_{22}$H$_{21}$ClFNO$_2$; C, 68.48; H, 5.49, N, 3.63; Cl, 9.19. Found: C, 68.21; H, 5.02; N, 3.31; Cl, 9.89.

EXAMPLE 2

2-Fluoro-5-(p-chlorobenzyl)-5,6,7,8,9,10-hexahydrocyclo hept[b]indole-7-carboxylic acid Step 1: Following the procedure of Example 1, using 3-oxo-cycloheptanecarbonitrile as the starting material 2-fluoro-5-(p-chlorobenzyl)-7-cyano-5,6,7,8,9,10-hexahydrocyclohept[b]indole was obtained as a solid. IR (KBr) 2235 cm$^{-1}$. 'H NMR (CDCl$_3$, 250 MHz) w 1.75–1.91 (m, 1H), 1.91–2.09 (m, 1H), 2.16–2.30 (m, 2H), 2.75–2.97 (m, 3H), 3.01–3.10 (m, 2H), 5.25 (d, J=17.5, 1H), 5.33 (d, J=17.5 Hz, 1H), 6.85–6.95 (m, 1H), 6.88 (d, J=8.5 Hz, 2H), 7.10 (d,d, J=4.0, 8.5 Hz, 1H), 7.17 (d,d, J=2.5, 9.5 Hz, 1H), 7.25 (d, J=8.5 Hz, 2H).

Step 2: To 300 mg of the nitrile from Step 1 in 3.0 mL of ethanol was added 3.0 mL of saturated aqueous Ba(OH)$_2$''8H$_2$O. The resultant mixture was heated at reflux for 24 h, cooled to room temperature and acidified with concentrated HCl. Ethyl acetate was added and the organic layer separated, washed with 1N HCl and twice with brine and dried over MgSO$_4$. Filtration and concentration gave a pale yellow oil which was purified by flash chromatography on silica gel (1:1 hexane-ethyl acetate) to give the title product, mp 185°–186° C. IR (KBr) 1705 cm$^{-1}$. 'H NMR (CDCl$_3$, 250 MHz) w 1.62–1.84 (m, 1H), 1.86–2.32 (m, 3H), 2.62–2.90 (m, 3H), 2.95–3.08 (m, 2H), 5.28 (d, J=18 Hz, 1H), 5.34 (d, J=18 Hz, 1H), 6.80–6.92 (m, 1H), 6.87 (d, J=8.5 Hz, 2H), 7.07 (d,d, J=4.5, 9.0 Hz, 1H), 7.16 (d,d, J=2.5, 9.5 Hz, 1H), 7.23 (d, J=8.5 Hz, 2H).

EXAMPLE 3

2-Fluoro-5-(p-chlorobenzyl)-5,6,7,8,9,10-hexahydrocyclohept[b]indole-6-acetic acid Step 1: Following the procedure of Example 1, but using ethyl 2-oxo-cycloheptaneacetate as the starting material, there was obtained ethyl 2-fluoro-5-(p-chlorobenzyl)-5,6,7,8,9,10-hexahydrocyclohept[b]indole-6-acetate. 'H NMR (CDCl$_3$, 250 MHz) w 1.18 (t, J=7.5 Hz, 3H), 1.32–1.65 (m, 2H), 1.70–2.10 (m, 4H), 2.48 9d,d, J=6.0, 14.5 Hz, 1H), 2.55–2.80 (m, 1H), 2.65 (d,d, J=7.5, 14.5 Hz, 1H), 2.98 (m, 1H), 3.52 (m, 1H), 3.98–4.14 (m, 2H), 5.28 (d, J=17.0 Hz, 1H), 5.48 (d, J= Hz, 1H), 6.80–6.90 (m, 1H), 6.85 (d, J=7.5 Hz, 2H), 7.06 (d,d, J=4.0, 8.5 Hz, 1H), 7.16 (d,d, J=3.0, 10.0 Hz, 1H), 7.21 (d, J=7.5 Hz, 2H).

Step 2: To 230 mg of the ester from Step 1 in 3.0 mL of ethanol was added 2.2 mL of 0.5M aqueous LiOH and the resultant mixture heated at reflux for 8 h. The reaction mixture was then cooled to room temperature, poured into ethyl acetate and acidified with concentrated HCl. The organic layer was separated, washed with 1N HCl and brine (2x) and dried over MgSO4. Concentration gave a yellow oil which solidified on standing. Trituration with hexane gave the title compound. IR (KBr) 1710 cm−1. 'H NMR (CDCl3, 250 MHz) w 1.35–1.70 (m, 2H), 1.80–2.12 (m, 4H), 2.50–2.65 (m, H), 2.54 (d,d, J=6.5, 16.0 Hz, 1H), 2.72 (d,d, J=8.5 Hz, 1H), 2.95–3.06 (m, 1H), 3.46–3.58 (m, 1H), 5.28 (d, J=7.5 Hz, 1H), 5.43 (d, J=7.5 Hz, 1H), 6.80–6.92 (m, 1H), 6.83 (d, J=8.0 Hz, 2H), 7.26 (d,d, J=4.0, 9.0 Hz, 1H), 7.16 (d,d, J=2.5, 10.0 Hz, 1H), 7.21 (d, J=8.0 Hz, 2H).

EXAMPLE 4

2,4-Difluoro-5(p-methylsulfonylbenzyl)-5,6,7,8,9,10-hexahydrocyclohept[b]indole-7-acetic acid Step 1: To 5.0 g of 1-(2,4-difluorophenyl)-hydrazinehydrochloride in 35 mL of 2-propanol containing 3.5 mL of sulfuric acid (conc) was added 5.4 g of methyl 3-oxo-cycloheptane-acetate. The reaction was refluxed under nitrogen for 2 days. After cooling, 40 mL of ether was added and the aqueous layer separated. The organic layer was consecutively washed with water, sodium bicarbonate solution and brine. The organic layer was dried over magnesium sulfate and evaporated to dryness. The crude product was passed through a silica gel bed eluting with 5% ethyl acetate/hexane to yield 4.0 g of a mixture of methyl and isopropyl esters.

Step 2: 4.0 g of esters from Step 1 was dissolved in 30 mL of methanol, 30 mL of sodium hydroxide (2.5N) was added and the mixture refluxed for 2 hours. After cooling the reaction mixture was diluted with 30 cc of water and washed with a (1:1) mixture of ether/hexane and the aqueous layer was acidified with HCl (1N). The resulting precipitate was filtered, washed with water and air dried to afford 3.5 g of 2,4-difluoro-5,6,7,8,9,10-hexahydrocyclohept[b]indole-7-acetic acid.

Step 3: To a cold solution (0° C.) of 3.5 g of acid from Step 2 in 75 mL of tetrahydrofuran was added dropwise 38.7 cc of a solution of KHMDS in toluene (0.684M) and the mixture stirred for 10 minutes. To the resulting cold (0° C.) solution was added dropwise 3.5 g of a solution of p-methylsulfonylbenzyl chloride in 10 mL of tetrahydrofuran. The reaction mixture was then stirred at room temperature for 6 hours. The reaction mixture was diluted with water and washed with Et2O. The aqueous layer was acidified with HCl (1N) and extracted with ethyl acetate. The organic layer was washed with brine, dried over magnesium sulfate and evaporated to dryness. The residue was triturated with a mixture of hexane/ethyl acetate (7:3) and filtered to yield the title product m.p. 200°–202° C.

EXAMPLE 5

2,4-Difluoro-5-(p-acetylbenzyl)-5,6,7,8,9,10-hexahydrocyclohept[b]indole-7-acetic acid Following the procedure of Example 4, Step 3 but using p-acetylbenzyl chloride, the title compound is obtained.

EXAMPLE 6

2,4-Difluoro-5-p-dimethylsulfamoylbenzyl)-5,6,7,8,9,10-hexahydrocyclohept[b]indole-7-acetic acid Following the procedure of Example 4, Step 3 but using p-dimethylsulfonamidobenzyl chloride, the title compound is obtained.

EXAMPLE 7

2-Fluoro-5-(p-methylsulfonylbenzyl)-5,6,7,8,9,10-hexahydrocyclohept[b]indole-6-acetic acid Following the procedure of Example 1, but using ethyl 2-oxo-cycloheptaneacetate and 1-(p-methylsulfonylbenzyl)-1-(p-fluorophenyl)hydrazine hydrochloride as starting materials, the title compound is obtained.

What is claimed is:

1. A compound of the formula:

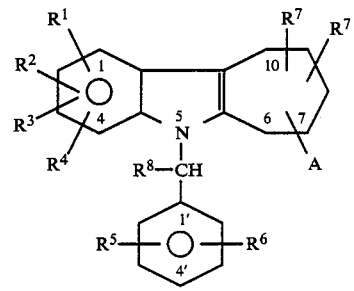

wherein:
A is $-(CR^9R^{10})_rR^{11}$;
$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) $-(CH_2)_nM$ wherein n is 0 to 3 and M is
 (a) $-C(O)R^{15}$;
 (b) $-C(O)NR^{17}R^{17}$;
 (c) $-CN$;
 (d) $-C(O)R^{16}$;
 (e) $-C(O)CH_2OH$ (hydroxymethyl ketone);
 (f) $-CF_3$;
 (g) $-R^{14}$;
 (i) $-OR^{12}$;
 (j) $-OC(O)R^{16}$;
 (k) $-OC(O)NR^{17}R^{17}$;
 (l) $-OC(O)OR^{18}$;
 (m) $-S(O)_2NR^{17}R^{17}$;
 (n) $-NR^{17}R^{17}$;
 (o) $-NHC(O)R^{16}$;
 (p) $-NHS(O)_2R^{13}$;
 (q) $-N_3$;
 (r) $-NO_2$; or
 (s) -halogen;
each $R^7$ is independently H or $C_1$ to $C_6$ alkyl;
each $R^8$ is independently H or $C_1$ to $C_6$ alkyl;

each $R^9$ is independently H or $C_1$ to $C_6$ alkyl;
each $R^{10}$ is independently H, OH, $C_1$ to $C_4$ alkoxy, or $C_1$ to $C_4$ alkyl;
$R^{11}$ is $-C(O)OR^{19}$;
each $R^{12}$ is independently H, $C_1$ to $C_6$ alkyl, benzyl, or $R^{14}$;
each $R^{13}$ is independently $C_1$ to $C_6$ alkyl, $CF_3$, or $R^{14}$;
each $R^{14}$ is independently phenyl, mono-substituted phenyl, or di-substituted phenyl wherein the substituents are independently, $C_1$ to $C_3$ alkyl, $C_1$ to $C_3$ perfluoroalkyl, $C_1$ to $C_3$ alkoxy, halogen, CN, $-C(O)OR^{15}$, or $-CH_2-C(O)OR^{15}$;
each $R^{15}$ is independently H, phenyl, benzyl or $C_1$ to $C_6$ alkyl;
each $R^{16}$ independently is H, $R^{13}$ or $(CH_2)_mC(O)OR^{15}$;
each $R^{17}$ is independently $R^{12}$;
each $R^{18}$ is independently $C_1$ to $C_6$ alkyl, benzyl or phenyl;
each $R^{19}$ is H, $C_1$ to $C_6$ alkyl, $R^{14}$, $R^{21}$, or $R^{22}$;
$R^{21}$ is $-CH_2-R^{14}$;
$R^{22}$ is $-CH_2-CH_2-R^{14}$
m is 0 to 4; and
r is 0 to 6.

2. A compound according to claim 1, wherein:
$R^1$, $R^2$, $R^3$, $R^4$, $R^5$ and $R^6$ are each independently selected from:
 (1) hydrogen;
 (2) alkyl having 1 to 6 carbon atoms;
 (3) alkenyl having 2 to 6 carbon atoms;
 (4) $-(CH_2)_nM$ wherein n is 0 or 1; and r is 1 to 6;

3. A compound according to claim 2, wherein:
A is attached to the 6- or 7- position;
n is 0;
$R^{11}$ is $-CO_2H$; and
r is 1 or 2.

4. A compound according to claim 3, wherein:
$R^1$, $R^2$, $R^3$ and $R^4$ are each independently selected from:
 (1) hydrogen;
 (2) alkyl having 1 to 6 carbon atoms;
 (3) M wherein M is
  (a) $-C(O)OR^{15}$;
  (b) $-C(O)NR^{17}R^{17}$;
  (c) $-CN$;
  (d) $-C(O)R^{16}$;
  (f) $-CF_3$;
  (g) $-OR^{12}$;
  (h) $-OC(O)R^{16}$;
  (i) $-S(O)_2NR^{17}R^{17}$;
  (j) $-N_3$; or
  (k) -halogen;
$R^5$ and $R^6$ are independently selected from:
 (1) hydrogen
 (2) alkyl having 1 to 6 carbon atoms
 (3) M wherein M is
  (a) $-C(O)OR^{15}$;
  (b) $-C(O)NR^{17}R^{17}$;
  (c) $-CN$;
  (d) $-C(O)R^{16}$;
  (e) $-CF_3$;
  (g) $-S(O)_2NR^{17}R^{17}$
  (h) $-N_3$;
  (u) $-NO_2$; or
  (j) -halogen;
each $R^{10}$ is independently H, or $C_1$ to $C_4$ alkyl; and
r is 1.

5. A compound according to claim 2 which is:
2-Fluoro-5-(p-chlorobenzyl)-5,6,7,8,9,10-hexahydrocyclohept[b]indole-7-acetic acid;
2-Fluoro-5-(p-chlorobenzyl)-5,6,7,8,9,10-hexahydrocyclohept[b]indole-10-acetic acid;
2-Fluoro-5-(p-chlorobenzyl)-5,6,7,8,9,10-hexahydrocyclohept[b]indole-7-carboxylic acid;
2-Fluoro-5-(p-chlorobenzyl)-5,6,7,8,9,10-hexahydrocyclo-hept[b]indole-6-acetic acid;
2,4-Difluoro-5-(p-acetylbenzyl)-5,6,7,8,9,10-hexahydrocyclohept[b]indole-7-acetic acid; or
2,4-Difluoro-5-(p-dimethylsulfamoylbenzyl)-5,6,7,8,9,10-hexahydrocyclohept[b]indole-7-acetic acid.

6. A compound according to claim 1, which is a pure optical isomer.

7. A compound according to claim 6, which is the (+)-isomer.

8. A compound according to claim 6, which is the (−)-isomer.

9. A method of inhibiting leukotriene synthesis in a mammal, which comprises administering to a mammal an effective amount of a compound of claim 1.

10. A pharmaceutical composition which comprises a compound of claim 2 and a pharmaceutically acceptable carrier.

* * * * *